United States Patent
Okada

(10) Patent No.: US 6,352,074 B1
(45) Date of Patent: Mar. 5, 2002

(54) BELT FOR FIXING PELVIS

(76) Inventor: Tadahisa Okada, 12-22, Hachiman-cho 3-chome, Higashi-Kurume-shi, Tokyo (JP)

(*) Notice: Subject to any disclaimer, the term of this patent is extended or adjusted under 35 U.S.C. 154(b) by 0 days.

(21) Appl. No.: 08/509,469

(22) Filed: Jul. 31, 1995

(30) Foreign Application Priority Data

Aug. 9, 1994 (JP) ............................................. 6-209106

(51) Int. Cl.$^7$ ............................................. A61F 5/24
(52) U.S. Cl. ..................... 128/98.1; 128/100.1; 606/201
(58) Field of Search ................. 606/201, 204; 128/96.1, 98.1, 121.1, 99.1, 101.1, 100.1, 106.1

(56) References Cited

U.S. PATENT DOCUMENTS

| | | | | |
|---|---|---|---|---|
| 691,143 A | * | 1/1902 | Hummel | 128/99.1 X |
| 713,450 A | * | 11/1902 | Kenyon | 128/121.1 X |
| 1,277,704 A | * | 9/1918 | Dillenbeck | 128/106.1 X |
| 3,526,221 A | * | 9/1970 | Garber | 128/99.1 X |
| 3,578,773 A | * | 5/1971 | Schultz | 128/78 |
| 4,243,028 A | * | 1/1981 | Puyana | 606/201 |
| 4,715,364 A | * | 12/1987 | Noguchi | 128/99.1 X |
| 5,078,728 A | * | 1/1992 | Giarratano | 606/201 X |
| 5,263,966 A | * | 11/1993 | Daneshvar | 606/201 |
| 5,372,575 A | * | 12/1994 | Sebastian | 606/201 X |
| 5,445,647 A | * | 8/1995 | Choy | 606/204 |

* cited by examiner

Primary Examiner—Michael H. Thaler
(74) Attorney, Agent, or Firm—Jordan and Hamburg LLP

(57) ABSTRACT

The present invention provides a belt for fixing a pelvis having a length which is adjustable to a user's physique. The belt suspends patches, made of rubber or soft pliable synthetic resin, on the right and left concavities located between the right and left projecting parts of the ilium and the right and left greater trochanter parts of the femurs.

6 Claims, 11 Drawing Sheets

BELT FOR FIXING PELVIS

BACKGROUND OF THE INVENTION

The present invention relates to a belt for fixing a pelvis which prevents back pain by preventing movement of the pelvis. The belt has suspending patches, into which sponge rubber or other cushion material is inserted, positionable between the right and left projecting part of the iliums and the right and left greater trochanter part of femurs.

SUMMARY OF THE INVENTION

The present invention provides a belt which users can wear for a long time without pain, without putting the belt on tightly because the present invention prevents movement of the belt from the concavities located between the right and left projecting part of the iliums and the right and left greater trochanter parts of the femurs. The prescribed and other objects and features of the present invention will be understood by reading carefully the following description in conjunction with accompanying drawings.

The drawings are illustrative and are not to be limitative of the scope of the present invention.

DESCRIPTION OF THE PRESENT INVENTION

Figure 1:
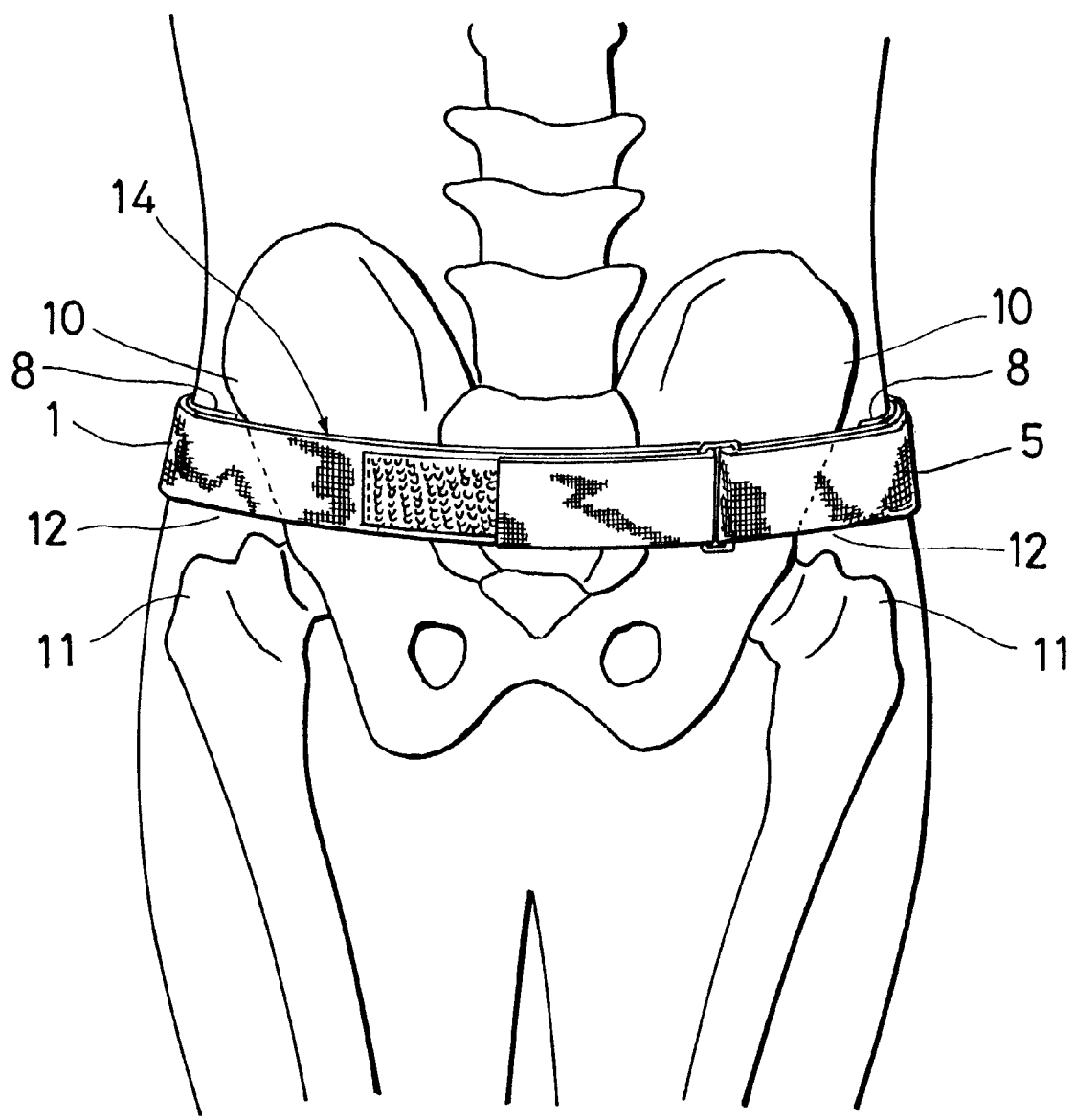
FIG. 1 is a illustration of a first embodiment of the present invention.
Figure 2:
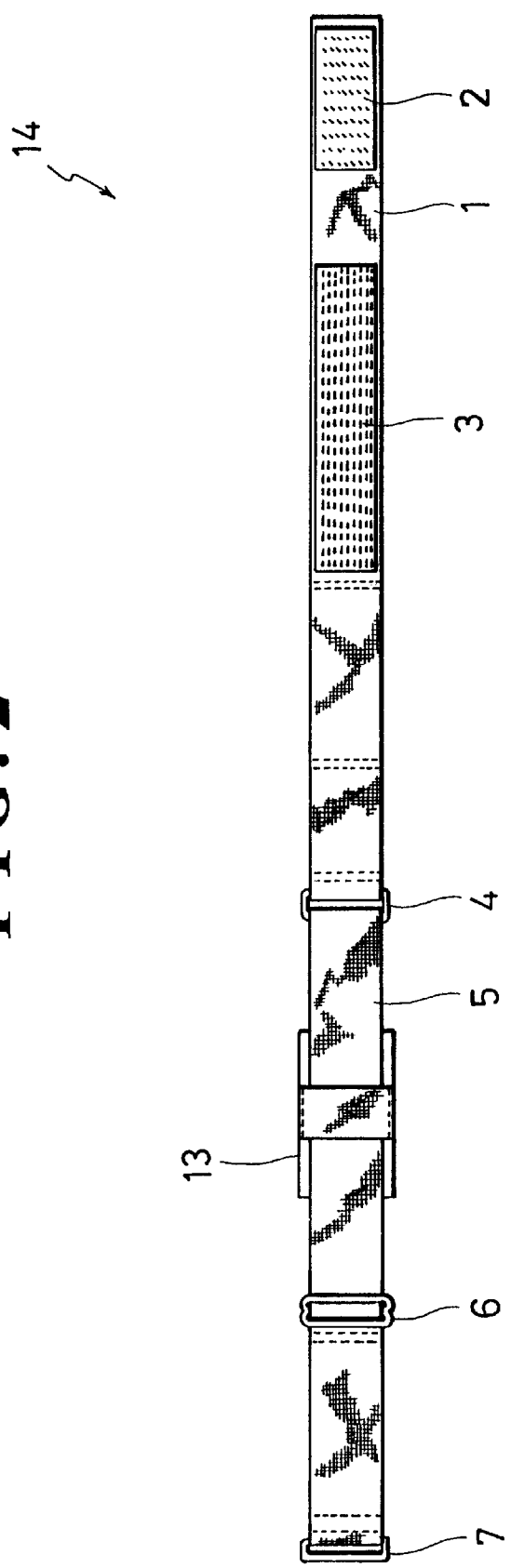
FIG. 2 is a front view showing the first embodiment of the present invention.
Figure 3:
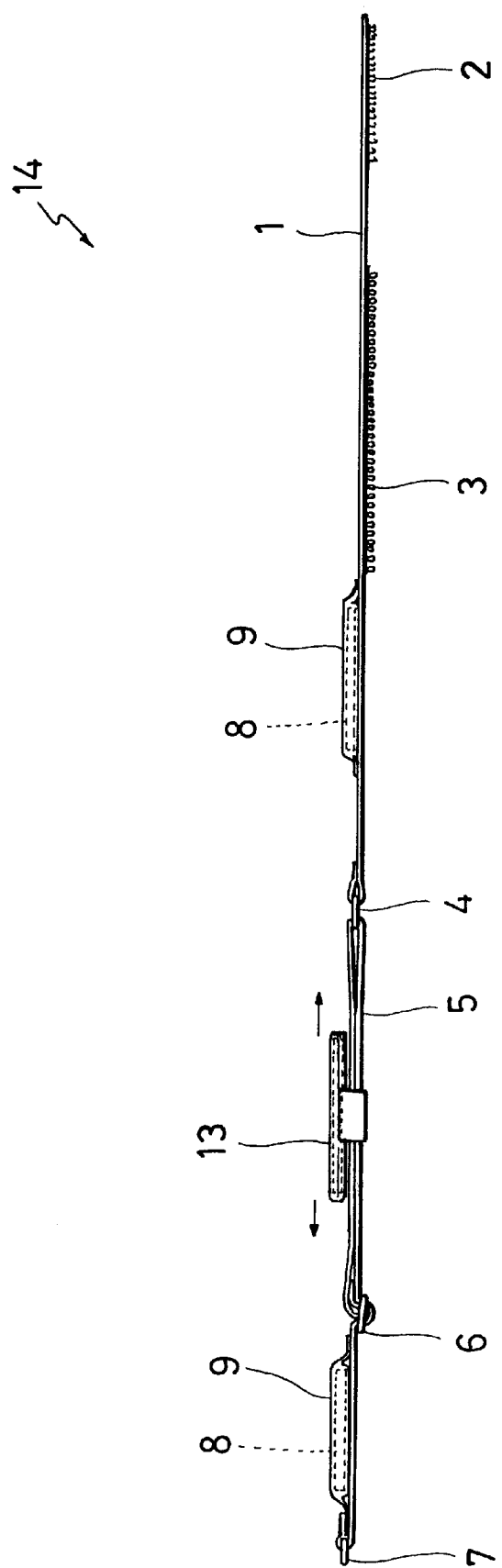
FIG. 3 is a plan view figure showing the first embodiment of the present invention.
Figure 4:
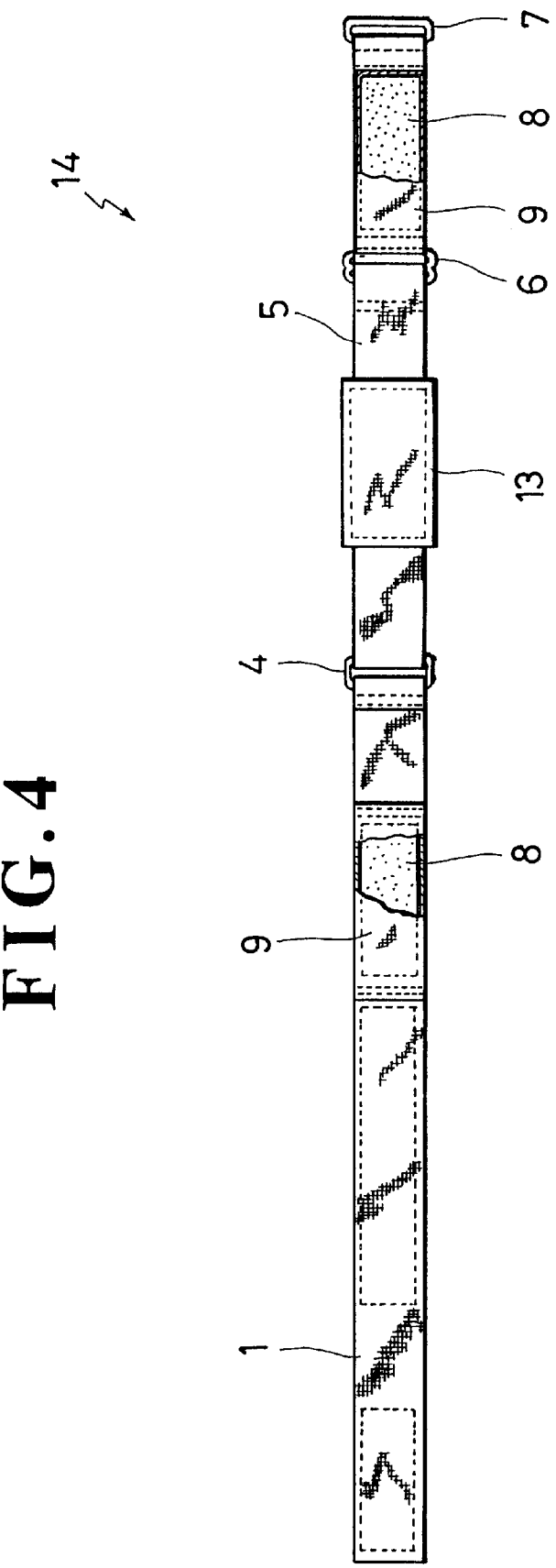
FIG. 4 is a back view figure showing the first embodiment of the present invention.
Figure 5:
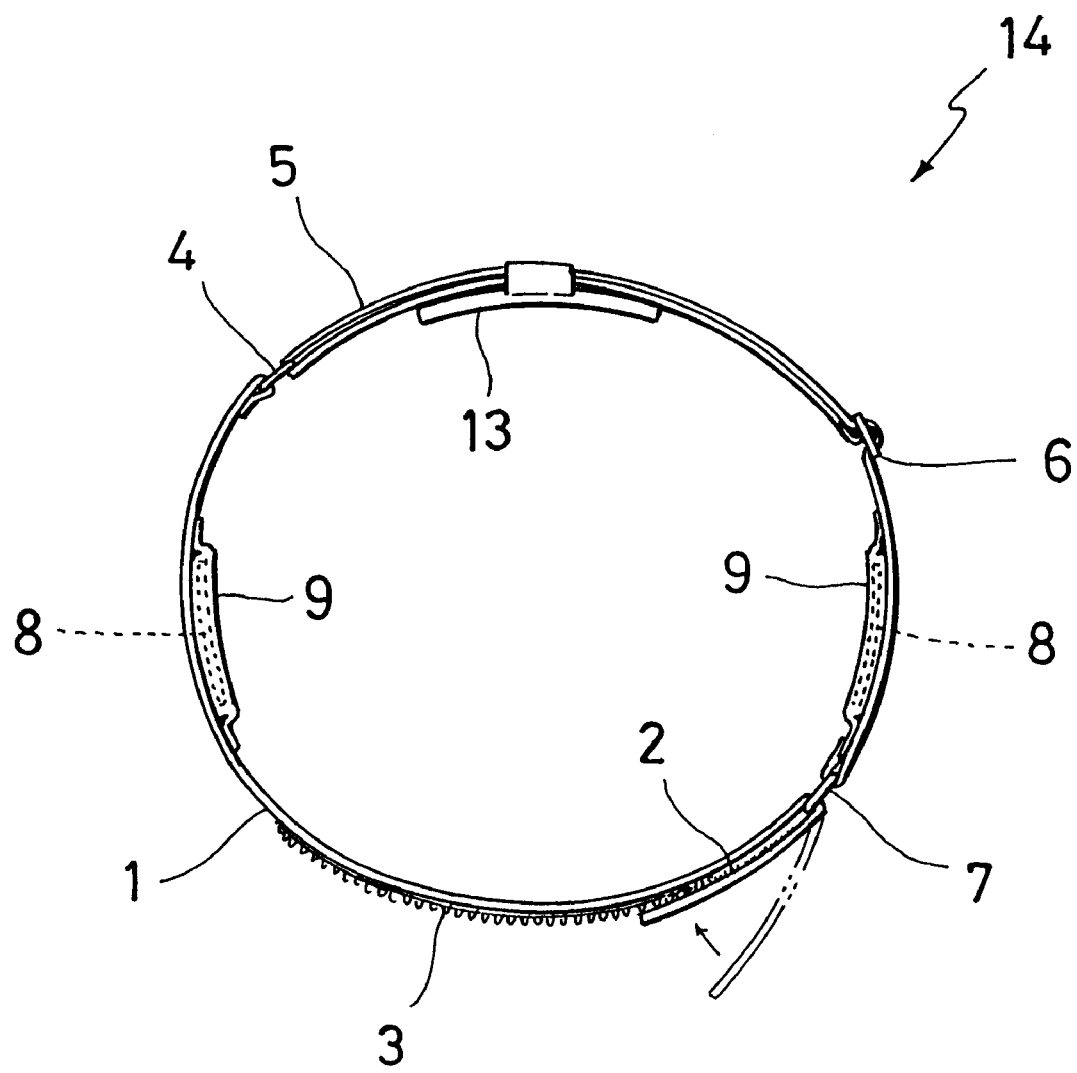
FIG. 5 is a plan view figure showing the first embodiment, which forms a ring, of the present invention.

A first embodiment of the present invention shown in FIGS. 1 to 5, has a fastening belt 1, which is made of cloth such as that used for seat belts. On a part near the tip of the fastening belt 1, a tip part side fastening material 2, hook and loop, is sewed and fixed and a center part side fastening material 3, engageable with the tip part fastening material 2, is sewed and fixed near a center part of the fastening belt 1.

A connecting ring 4 is sewed and fixed on an end part of the fastening belt 1.

An adjustable belt 5, made of the same material as fastening belt 1, is passed through the fastening ring 4. On a rear part of the adjustable belt 5, a length adjusting metal adjustment fitting 6 is installed, and on a tip part of the adjustable belt 5, a connecting ring 7 is sewed and fixed.

Suspending patches 8, on the right and left, are held in bags 9 which are sewed and fixed on the rear part of the fastening belt 1 and the rear part of the adjustable belt 5. The suspending patches 8 prevent the fastening and adjusting belt 1 from moving away from right and left concavities 12 located between the right and left projecting part of the iliums and the right and left greater trochanter part of the femurs. The suspending patches 8 are formed from hard rubber, pliable synthetic resin, or other material having elasticity.

A back side patch 13 is slidably installed on the fastening belt 1 or the adjustable belt 5 as required. The back side patch 13 is located in a space defined between user's body and the fastening belt 1 and stabilizes the position of the belt 14.

The belt 14 is adjusted by adjusting the right and left suspending patches 8 to the concavities 12 located between the right and left projecting part of the iliums 10 and the right and left greater trochanter part of the femurs 11. The suspending patches 8 are located by sliding the adjustment fitting 6 to adjust the length of the adjustable belt 5.

In an adjusted condition, the right and left suspending patches 8 suspend on the concavities 12 over briefs, and the tip part of the fastening belt 1 is passed through the connecting ring 7 and the fastening materials 2 and 3 are joined together to fasten the belt 14 with little looseness. In this condition, forces of separation are restrained by the belt 14, and even if a user moves, the suspending patches 8 prevent movement of shifting of the belt 14.

Other embodiments of the present invention will now be described referring to FIGS. 6 to 16. Throughout the drawings of the embodiments, like components are denoted by like numerals as of the first embodiment and will be explained in no further detail.

Figure 6:
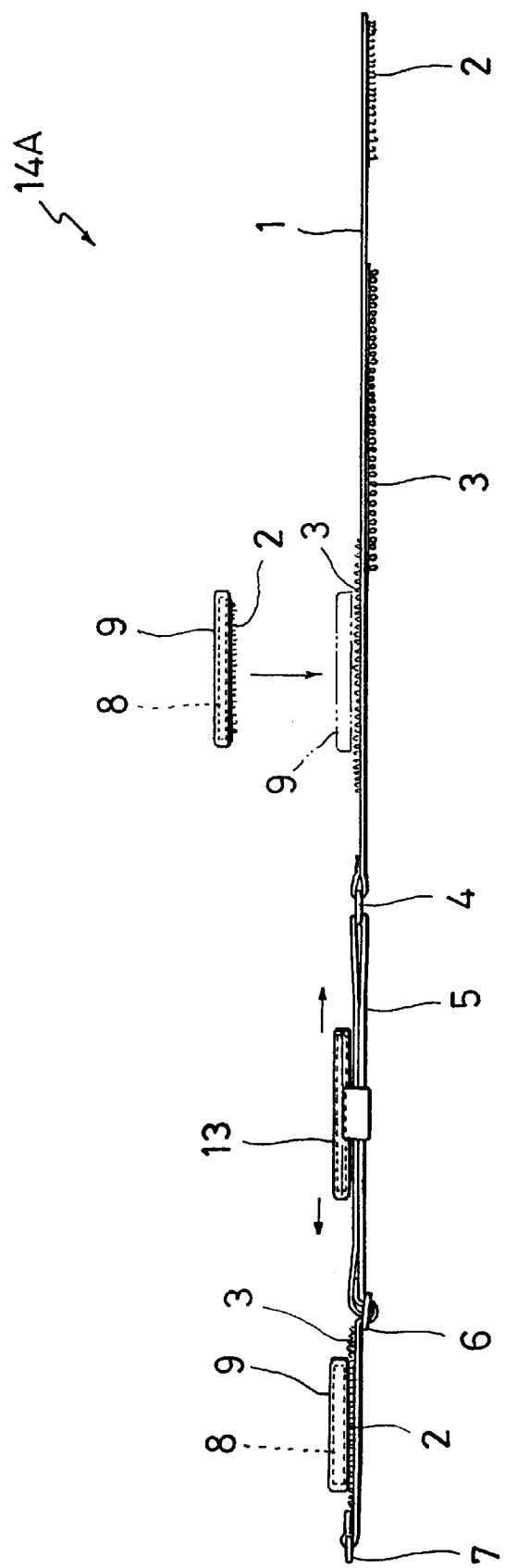
FIG. 6 is a plan view figure showing a second embodiment of the present invention.
Figure 7:
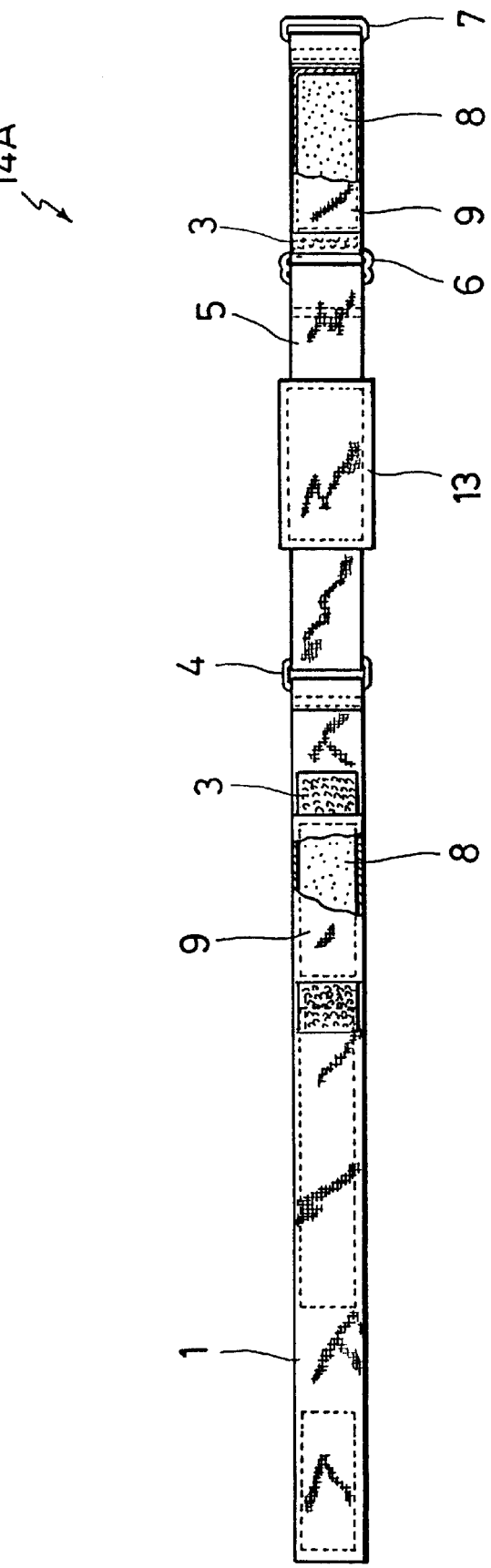
FIG. 7 is a back view figure showing the second embodiment of the present invention.
Figure 8:
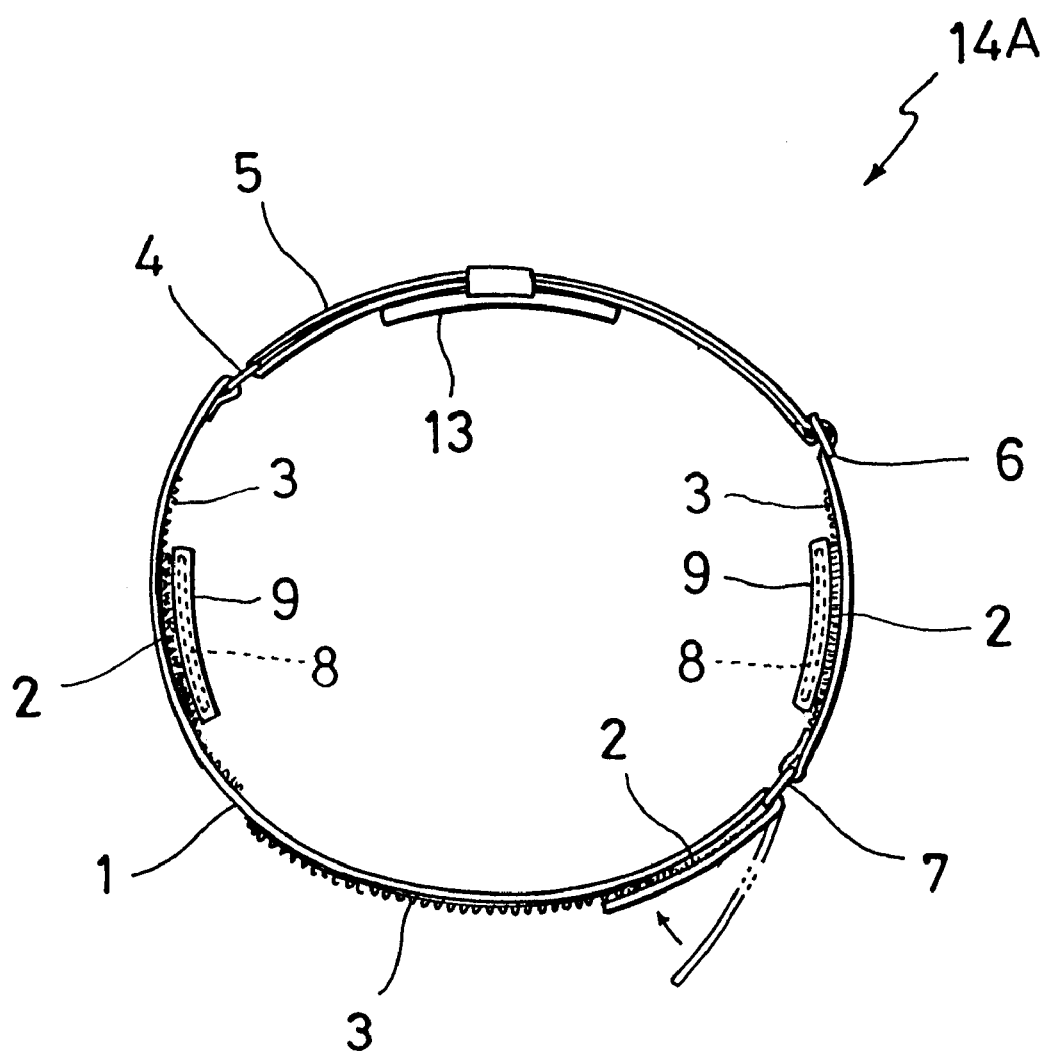
FIG. 8 is a plan view figure showing the second embodiment, which forms a ring, of the present invention.

A second embodiment of the present invention is shown in FIG. 6 to FIG. 8. A difference from the first embodiment of the present invention is that the right and left suspending patches 8, stored in the bags 9, are removably fastened by hook and loop fasteners 2 and 3 on the fastening belt 1 and adjustable belt 5. The belt for fixing a pelvis 14A has the same effect as the first embodiment of the present invention above, and it is possible to move and adjust the locations of the suspending patches 8.

Figure 9:
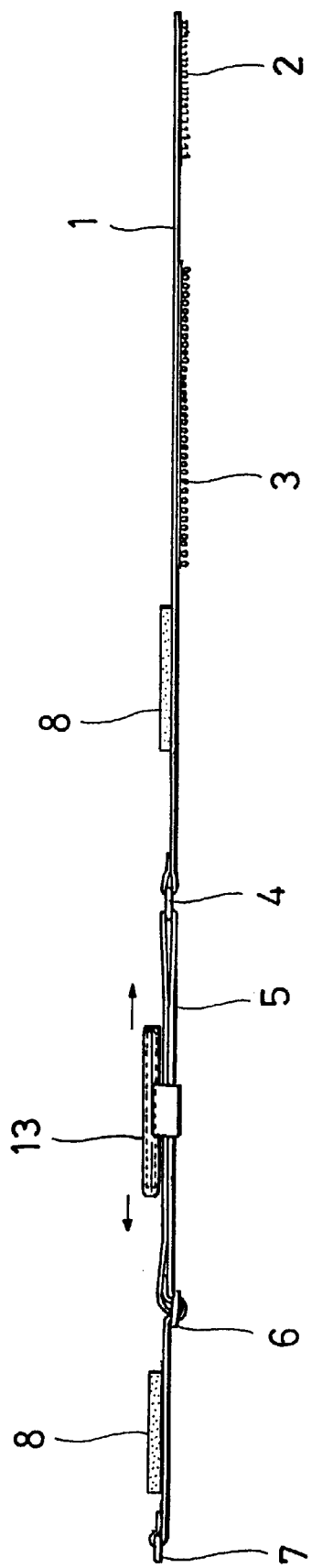
FIG. 9 is a plan view figure showing a third embodiment of the present invention.
Figure 10:
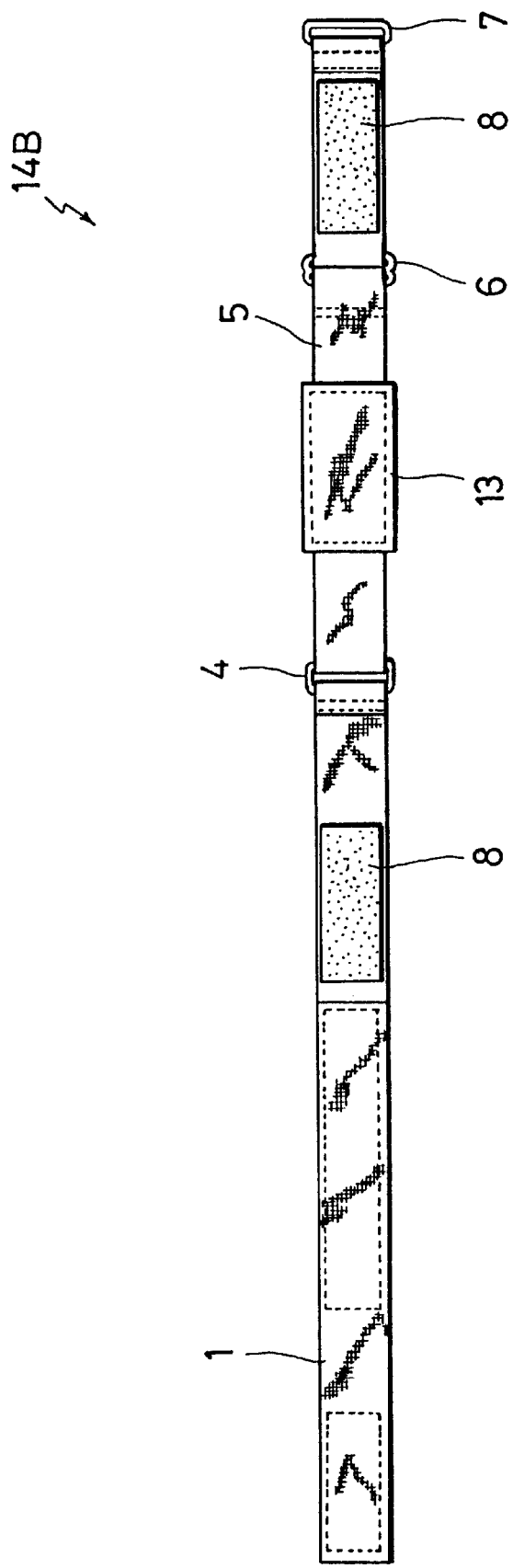
FIG. 10 is a back view figure showing the third embodiment of the present invention.
Figure 11:
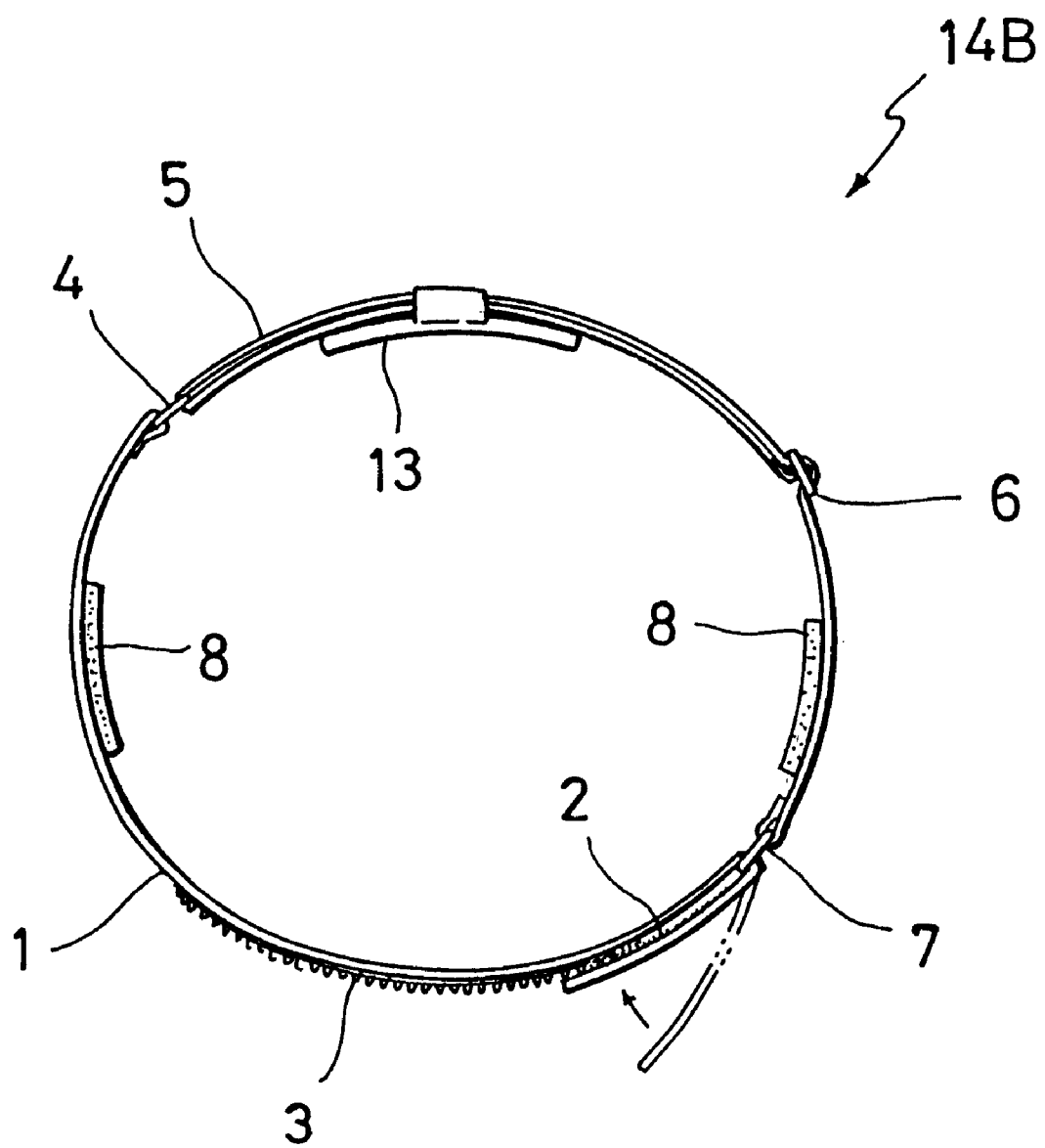
FIG. 11 is a plan view figure showing the third embodiment, which forms a ring, of the present invention.

A third embodiment of the present invention is shown in FIGS. 9 to 11. A difference from the first embodiment of the present invention is that the right and left suspending patches 8 are directly fixed by an adhesive or sewed to the adjustable belt 5. The belt 14B, has the same effect as the first embodiment of the present invention.

Still further, double sided adhesive tape may be applied to the adjustable belt or fastening belt of each embodiment of the present invention. When users put on the belt, the users may attach and fix the double sided adhesive tape on clothing to prevent the fastening belt or the adjustable belt from moving.

As set forth above, the advantages of the present invention are as follows:

The belt for fixing pelvis has the fastening belt with fastening materials thereon making it possible to locate and install over the concavities located between the right and left projecting part of iliums and the right and left greater trochanter part of femurs, thus fixing the belt at an optional location. The adjustable length metal fittings and the installation ring are installed on the rear part of the fastening belt. The connecting suspending ring installed on the tip part of the adjustable belt, the right and left suspending patches, which can be suspended on the concavities located between the right and left projecting part of iliums and the right and left greater trochanter part of femurs above, are installed inside of the installation belt and the adjustable belt. Thus, it is possible to suspend the right and left suspending patches on the concavities located between the right and left projecting part of iliums and the right and left greater trochanter part of femurs above.

Therefore, movement of the belt while user is putting the belt on is prevented. The pelvis is prevented from separating and back pain is prevented.

Thus, it is possible to use the belt without regard for size because the length of the adjustable belt is adjusted by the adjustable length metal fittings.

Therefore, it is not necessary to have numerous sizes of belts.

Soft pliable synthetic resin or rubber is used for the right and left suspending patches; therefore, no sense of illfit or pain exists even if worn for a long time. Moreover, it is light, and can be used comfortably.

The belt for fixing the pelvis is simple so everyone can put it on as putting a belt on pants, and it is possible to manufacture at low cost relatively.

What is claimed is:

1. A pelvis fixing belt to be worn by a user, comprising:

a belt member, for wrapping around a pelvis of the user, having first and second ends, an inside surface facing the pelvis and an outside surface opposite said inside surface;

connecting means at said first and second ends for adjustably connecting said belt member around said pelvis so as to accommodate varying pelvic circumferences;

first and second cushion members disposed on said inside surface of said belt member at first and second regions of said belt member corresponding to first and second concavities in a body of the user respectively located between right and left projecting parts of iliums of the user and respective right and left greater trochanter projections of femurs of the user; and said first and second cushion members being configured to engage in said first and second concavities, respectively, so as to fix a location of the belt member on the user in alignment with said first and second concavities.

2. The pelvis fixing belt of claim 1 further comprising:

said belt member including first and second belt portions having said first and second cushion members disposed respectively thereon; and second connecting means for adjustably connecting said first and second belt portions such that a length of at least one of said first and second belt portions is variable to position said first and second cushion members in said first and second concavities.

3. The pelvis fixing belt of claim 2 further comprising one of said first and second belt portions having a back pad on said inside surface thereof which is positionable to fit against a back of the user.

4. The pelvis fixing belt of claim 1 further comprising said belt member having a back pad on said inside surface thereof which is positionable to fit against a back of the user.

5. A pelvis fixing belt to be worn by a user, comprising.

a belt member, for wrapping around a pelvis of the user, having first and second ends, an inside surface facing the pelvis and an outside surface opposite said inside surface;

said belt member including first and second belt portions having first and second cushion members disposed respectively thereon on said inside surface of said belt member at first and second regions of said belt member corresponding to first and second concavities in a body of the user respectively located between right and left projecting parts of iliums of the user and respective right and left greater trochanter projections of femurs of the users;

said first and second cushion members being configured to engage in said first and second concavities, respectively, so as to fix a location of the belt member on the user in alignment with said first and second concavities;

connecting means at said first and second ends for adjustably connecting said belt member around said pelvis so as to accommodate varying pelvic circumferences; and second connecting means for adjustably connecting said first and second belt portions such that a length of at least one of said first and second belt portions is variable to position said first and second cushion members in said first and second concavities.

6. The pelvis fixing belt of claim 5 further comprising one of said first and second belt portions having a back pad on said inside surface thereof which is positionable to fit against a back of the user.

\* \* \* \* \*